US010538734B2

(12) United States Patent
Lauraeus et al.

(10) Patent No.: US 10,538,734 B2
(45) **Date of Patent: *Jan. 21, 2020**

(54) COMPOSITION FOR EMBEDDED MICROBIAL CULTURE

(71) Applicant: UPM-KYMMENE CORPORATION, Helsinki (FI)

(72) Inventors: Marko Lauraeus, Vihti (FI); Antti Laukkanen, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 14/368,018

(22) PCT Filed: Dec. 18, 2012

(86) PCT No.: PCT/FI2012/051266

§ 371 (c)(1),
(2) Date: Jun. 23, 2014

(87) PCT Pub. No.: WO2013/093199

PCT Pub. Date: Jun. 27, 2013

(65) Prior Publication Data

US 2015/0010980 A1 Jan. 8, 2015

(30) Foreign Application Priority Data

Dec. 22, 2011 (FI) ..................................... 20116314

(51) Int. Cl.

| | |
|---|---|
| ***C12N 1/22*** | (2006.01) |
| ***C12N 11/12*** | (2006.01) |
| ***C12N 1/20*** | (2006.01) |

(52) U.S. Cl.

CPC ................. *C12N 1/22* (2013.01); *C12N 1/20* (2013.01); *C12N 11/12* (2013.01)

(58) Field of Classification Search

CPC ............. C12N 1/22; C12N 1/20; C12N 11/12
See application file for complete search history.

(56) References Cited

U.S. PATENT DOCUMENTS

| | | | | |
|---|---|---|---|---|
| 2,978,446 | A | 4/1961 | Battista et al. | |
| 5,055,130 | A * | 10/1991 | Arnold ...................... | C22B 3/18 435/838 |
| 5,254,471 | A | 10/1993 | Mori et al. | |
| 9,593,304 | B2 * | 3/2017 | Laukkanen .......... | C12N 5/0062 |
| 2007/0172938 | A1 | 7/2007 | Deguchi et al. | |
| 2008/0146701 | A1 * | 6/2008 | Sain ...................... | B82Y 30/00 524/9 |
| 2011/0015387 | A1 * | 1/2011 | Schuth ................... | C08B 1/003 536/124 |
| 2013/0344036 | A1 * | 12/2013 | Yliperttula ............... | A61K 9/06 424/93.7 |

FOREIGN PATENT DOCUMENTS

| | | | | |
|---|---|---|---|---|
| WO | 2005/083056 | A1 | 9/2005 | |
| WO | 2009126980 | A1 | 10/2009 | |
| WO | WO 2010135234 | A2 * | 11/2010 | ............... C12N 1/20 |
| WO | 2012056109 | A2 | 5/2012 | |
| WO | WO 2012056109 | A2 * | 5/2012 | ............... A61K 9/06 |

OTHER PUBLICATIONS

Ramirez-Arcos, S et al. A thermophilic nitrate reductase is responsible for the strain specific anaerobic growth of Thermus thermophilus HB8. Biochimica et Biophysica Acta. 1998. 1396: 215-227.*
'Matrix' in: Oxford Dictionaries [online]. 2018. [retrieved on Mar. 12, 2018]. Retrieved from the Internet: <URL: https:// en.oxforddictionaries.com/definition/rnatrix>. (Year: 2018).*
Cassidy, MB et al. Environmental applications of immobilized microbial cells: a review. Journal of Industrial Microbiology. 1996. 16: 79-101. (Year: 1996).*
Tsudome et al., "Versatile Solidiied Nanofibrous Cellulose-Containing Media for Growth of Extremophiles", Applied and Environmental Microbiology, 2009, vol. 75, No. 13, pp. 4616-4619.
Bhattacharya et al., "Nanofibrillar cellulose hydrogel promotes three-dimensional liver cell culture", Journal of Controlled Release, 2012, vol. 164, pp. 291-298.
Czaja et al., "The Future Prospects of Microbial Cellulose in Biomedical Applications", Biomacromolecules, 2007, vol. 8, No. 1, pp. 1-12.
Deguchi et al., "Preparation and characterisation of nanofibrous cellulose plate as a new solid support for microbial culture", Soft Matter, 2007, vol. 3, pp. 1170-1175.
International Search Report, dated Apr. 22, 2013, from corresponding PCT application.
M. Pääkkö, et al., "Enzymatic Hydrolysis Combined with Mechanical Shearing and High-Pressure Homogenization for Nanoscale Cellulose Fibrils and Strong Gels", Biomacromolecules, 2007, 8, 1934-1941.
Biseibutsu Kougaku Gijutsu Handbook (Microbial Engineering Technology Handbook) Asakura Publishing Co., Ltd, 1990, 1st Edition; p. 6-8.
Notice of Reasons for Refusal from corresponding Japanese Patent Application No. 548121/2014, dated Nov. 8, 2016 with English Translation.
Ung-Jin Kim, et al., "Thermal decomposition of dialdehyde cellulose and its nitrogen-containing derivatives", Thermochimica Acta, 369, (2001), 79-85.
The Merck Index: An encyclopedia of chemicals, drugs, and biologicals, 1996.
Microbiology, Basic Master series, Omsha, 2006, 1st Edition, p. 55.
Notice of Reasons for Refusal from corresponding Japanese Patent Application No. 548121/2014, dated Aug. 15, 2017 with English Translation (14 pages).

(Continued)

*Primary Examiner* — Renee Claytor
*Assistant Examiner* — Susan E. Fernandez
(74) *Attorney, Agent, or Firm* — Nixon Peabody LLP

(57) ABSTRACT

Disclosed is a composition for embedded three-dimensional microbial culture, the composition including nanofibrillar cellulose and at least one nutrient source. Also disclosed is a method for the manufacture of a composition for embedded three-dimensional microbial culture, the method including the steps of providing nanofibrillar cellulose, mixing the nanofibrillar cellulose with water and at least one nutrient source and optional additives to obtain a mixture, and optionally drying the mixture.

10 Claims, 5 Drawing Sheets

(56) References Cited

OTHER PUBLICATIONS

Pitkanen, M. et al.; "Nanofibrillar cellulose—in vitro study of cytotoxic and genotoxic properties"; TAPPI, 2010 International Conference on Nanotechnology for the Forest Products Industry; Sep. 27-29, 2010 (16 pages).
Tetsuo Kondo; "New Aspects of Cellulose Nanofibers"; Journal of the Japan Society of Wood Technology, vol., 54, No. 3, pp. 107-115, with English translation; 2008 (17 pages).
Decision of Declining Amendments—from Japanese Patent Application No. 548121/2014, dated Apr. 3, 2018 with English Translation.
Notice of Reasons for Refusal—from Japanese Patent Application No. 548121/2014, dated Apr. 3, 2018 with English Translation.
Journal of Textile Engineering, 1997, vol. 50, No. 4, p. 7-11.

* cited by examiner

COMPOSITION FOR EMBEDDED MICROBIAL CULTURE

FIELD OF THE INVENTION

The invention relates to new applications of fibril cellulose in the field of microbiology. Particularly the invention relates to a composition comprising fibril cellulose for embedded microbial culturing methods, including anaerobic and semi-anaerobic microbial culturing methods. The invention also concerns a three-dimensional matrix comprising fibril cellulose for embedded microbial culturing methods including anaerobic and semi-anaerobic microbial culturing methods. The invention further relates to the use and a method for use of fibril cellulose in a matrix for embedded microbial culturing methods, and to a method for the embedded microbial culture.

BACKGROUND

Hydrogel materials are used in culturing tasks where hydrophilic supporting material is needed, for example agar type hydrocolloids are widely used in plant cell, bacterial, and fungi culturing for various microbiological purposes.

Agar is a linear and non-ionic polysaccharide consisting of D-galactose and 3,6-anhydro-L-galactose and it is produced from seaweeds. In solid cultures suspensions of microbial cells are spread onto the surface of the agar hydrogel, typically containing 1.5 wt % of agar, and nutrient fluid. The microorganisms grow and form macroscopic colonies, which can be separated and pure cultures may be obtained. The use of solid agar plates provides two-dimensional growth and requires mechanical separation by cutting.

Several alternatives for the use of agar plates have been proposed, for example gellan gum produced by *Pseudomonas elodea*. Gellan gum is soluble in hot water, forms a stiff gel upon cooling and shows improved stability at higher temperatures. Hydrogels based on gellan gum are very sensitive to nutrients and additives and require careful formulation of the medium. Also the use of solid gellan gum plates provides two-dimensional growth.

In Deguchi, S. et al. Preparation and characterisation of nanofibrous cellulose plate as a new solid support for microbial culture, *Soft Matter,* 2007, Vol. 3, No. 9, s. 1170-1175 a nanofibrous cellulose plate is suggested for solid culture of microorganisms where the cellulose was obtained by dispersing microcrystalline cellulose in an aqueous saturated solution of $Ca(SCN)_2$ to form a complex between cellulose and calcium thiocyanate ions, followed by dissolving the cellulose by heating, and obtaining a viscous solution. Said solution was then poured into a culture dish, allowed to solidify and followed by washing with methanol and water. After washing the gelation was fixed. The optimal cellulose concentration in the plates was between 2 and 3 wt %. The pores of the plates were filled with an appropriate nutrient fluid. *E. coli, B. subtilis*, and *S. cerevisiae* as well as *T. thermophilus* grew on the cellulose plates.

U.S. Pat. No. 5,254,471 discloses a carrier for culturing cells, made of ultra fine fibers. WO 2009/126980 discloses cellulose-based hydrogel, which contains cellulose exhibiting an average degree of polymerization of 150-6200.

Anaerobic and semi-anaerobic microbial culture techniques are typically regarded as challenging to perform with current growth media and plating systems. There are several microbe species having strong sensitivity to oxygen, such as Clostridial species, and thus it is essential to remove oxygen from the cultivation environment. Further, microbial colonies are typically cut from the culturing media and thereafter the culturing media has to be removed.

Anaerobic and semi-anaerobic microbes are often cultured in embedded systems. In said systems, for example paraffin embedded cultures of microbes have been proposed, as well as cultures between two agar layers or plates.

In connection with microbial culture, fermentation and microbial sample storage, detection, enumeration and quantification of microbes based on techniques where real-time polymerase chain reaction (PCR) is carried out, are today widely used. In PCR the microbes are broken down to release their DNA, and the DNA is thereafter quantified by using specific oligonucleotide primers, thermostable DNA polymerase and appropriate thermal cycler. Many materials, especially polymeric materials inhibit the PCR reactions and make microbial quantification unreliable. Typically such materials are used as fermentation media, culturing media, sample storage matrix, fermentation enhancers, and transportation matrix, which interfere with the detection and quantification procedures.

Existing three dimensional (3D) cell culture biomaterials do not allow transferring the hydrogel matrix for example with a needle without seriously damaging the cultured cells.

Thus there exists a need to provide improved compositions, matrix and methods for embedded microbial culture including anaerobic and semi-anaerobic methods, where the disadvantages of the materials of state of the art can be avoided or at least substantially decreased.

SUMMARY

The present invention is based on studies on hydrogels composed of fibril cellulose, which is dispersed in an aqueous environment. The fibres of fibril cellulose are highly hydrophilic due to hydroxyl functionalities of cellulose polymers and partly covered with hemicellulose polysaccharides.

The invention is directed to a composition comprising fibril cellulose for embedded microbial culture, particularly to a composition comprising fibril cellulose for embedded 3D microbial culture. Said composition is particularly suitable for anaerobic and semi-anaerobic microbial culture of microbes, such as bacteria, molds, yeasts and protozoa. Microbial culture is understood to include here any kind of culture and fermentation processes.

The invention is also directed to a method for the manufacture of a composition for embedded microbial culture, said method comprising the steps of

- providing fibril cellulose,
- mixing said fibril cellulose with water and optional nutrient sources and additives to obtain a mixture/composition.

The composition is suitably transferred or placed to an environment for embedded 3D culture of microbes.

The invention is directed to the use of the composition in a matrix for embedded 3D microbial culture.

The invention is further directed to a 3D matrix for embedded microbial culture, said matrix comprising a composition comprising fibril cellulose, optional nutrient sources and additives, and living microbe cells.

Said matrix may also be used as immobilization matrix in fermentation processes and for storage and transportation of microbes, particularly where microbe is selected from bacteria, molds, yeasts and protozoa.

The invention further relates to the use and a method of using fibril cellulose in a 3D matrix for embedded microbial culture, said method comprising the steps of providing living microbe cells where the microbe is selected from bacteria, molds, yeasts and protozoa, providing a composition comprising fibril cellulose and optional nutrient sources and optional additives, incorporating said microbe cells in the composition to provide a three-dimensional arrangement.

The invention is further directed to a method for embedded culture of microbes, particularly for 3D embedded culture of microbes, said method comprising the steps of providing living microbe cells, where the microbe is selected from bacteria, molds, yeasts and protozoa, contacting the cells with a composition comprising fibril cellulose, culturing the cells within said matrix in three-dimensional arrangement in an environment for embedded microbial culture.

The present invention is based on the use of fibril cellulose in 3D embedded microbial culture matrix.

Microbial cells divide on and in the media, start to proliferate and cell clusters start to grow spontaneously without the accumulation of cells on the bottom of the cell culture platform. The homogenous dividing of the cells in the fibril cellulose is a prerequisite for the material to function as 3D microbial culture media.

Fibril cellulose is inert and gives no fluorescent background and thus it does not interfere in analysis. The media comprising fibril cellulose can be injected, dispersed and pumped. This property is explained by the rheological properties of hydrogels based on fibril cellulose. The injection can be performed so that the cells stay stable inside the matrix and are homogeneously distributed in the matrix after injection.

Accordingly, the present invention provides means for embedded culture and fermentation of microbes using a composition comprising fibril cellulose, wherein the composition is in a form of a hydrogel. Said culture method is particularly suitable for anaerobic and semi-anaerobic culture systems, both in small scale, larger industrial fermentation scale and very large scale, such as in bioleaching processes.

The characteristic features of the invention are presented in the appended claims.

DEFINITIONS

Figure 1:
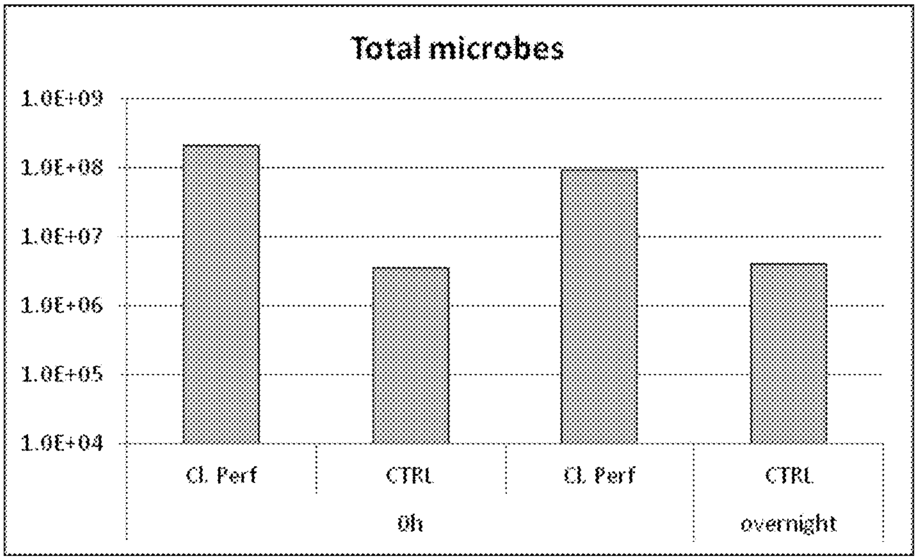
FIG. 1 illustrates graphically reference bacterial *Clostridium perfringens* cell numbers in the beginning (0 h) and after overnight incubation on fibril cellulose.

Unless otherwise specified, the terms, which are used in the specification and claims, have the meanings commonly used in the field of microbiology and macromolecules. Specifically, the following terms have the meanings indicated below.

"Embedded microbial culture" is understood here to mean 3D microbial culture where the microbes, which are cultured, are partly or totally embedded in the culture media or matrix comprising fibril cellulose. Embedded microbial culture is understood to include here anaerobic and semi-anaerobic culture of microbes where the microbes have no or limited access to oxygen.

"Microbial culture" refers here to any culture or fermentation of microbes, including bioleaching processes.

"Anaerobic culture" means here microbial culture in an environment not containing oxygen. Anaerobic culture is particularly suitable for example for obligate anaerobes.

"Semi-anaerobic culture" refers here to microbial culture in an environment containing limited amounts of oxygen. Said culture is particularly suitable for example for aerotolerant organisms and facultative aerobes.

The microbes refer here to molds, yeasts, bacteria and protozoa. Examples of such microbes are particularly species belonging to any one of the groups obligate anaerobes, aerotolerant organisms and facultative aerobes.

The term "media" or "culture media" refers here to nutritional environment, which is necessary for any microbe to be propagated. The biochemical (nutritional) environment is made available as a culture medium. Culture media are employed in the isolation and maintenance of pure cultures of microbes and are also used for identification of for example bacteria according to their biochemical and physiological properties.

The term "bioleaching" or "bioheapleaching" means here a bio-oxidation process where bacteria are utilized to convert insoluble metal compounds in ores, containing metals such as copper, gold, zinc, cobalt, nickel and uranium, to water-soluble metal compounds, which can further be converted to elemental metals.

As used herein, the term "fibril cellulose" is understood to encompass all microfibrillated celluloses (MFC) and nanocelluloses. Further, there are several other widely used synonyms for fibril cellulose. For example: cellulose nanofiber, nanofibrillated cellulose (CNF), nanofibrillar cellulose (NFC), nano-scale fibrillated cellulose, microfibrillar cellulose, or cellulose microfibrils.

In addition, fibril cellulose produced by certain microbes has also various synonyms, for example, bacterial cellulose (BC), microbial cellulose (MC), biocellulose, nata de coco (NDC), or coco de nata (CDN).

DETAILED DESCRIPTION OF THE INVENTION

It was surprisingly found that a composition comprising fibril cellulose is suitable for embedded 3D microbial culture, particularly when the fibril cellulose is in the form of hydrogel. Said composition may be used in a matrix for embedded microbial culture where it is essential to provide anaerobic or semi-anaerobic conditions for microbial growth. Thus the invention provides means for embedded microbial culture as well as a method for embedded culture of microbes, particularly for anaerobic and semi-anaerobic culture of microbes.

The microbe cells divide in the composition, start to proliferate and the cell clusters start to grow spontaneously. The cells divide homogeneously in the culture media comprising fibril cellulose. The homogenous dividing of the cells in the fibril cellulose is a prerequisite for the material to function in embedded 3D microbial culture. Embedded culture enables the culturing with limited amounts of air or oxygen as well as without air or oxygen, if desired.

The hydrogel structure enables the microbes to grow and divide uniformly in the gel matrix without sedimentation or accumulation on the bottom of a vessel, such as a fermentation vessel. The hydrogel is also able to stabilize nutrients, substrates and any other components included in the composition or in the fermentation media and prevents possible sedimentation thereof. The properties of the hydrogel may be adjusted according to the needs to more or less viscous by selecting a suitable grade of fibril cellulose or by varying the amount of fibril cellulose in the hydrogel.

The above features are valuable in small scale culture as well as in larger scale culture in fermentation vessels, and particularly in large bioleaching processes where the fibril cellulose hydrogel provides optimal growth environment for the microbes by preventing the solid mineral/stone substrate from sedimenting. The growth media keeps more homogeneous and the bioleaching process keeps more stable and more easily controllable.

The fibril cellulose may be obtained from any plant based cellulose raw material or it may originate from cellulose-producing micro-organisms i.e. microbial cellulose.

The term "cellulose raw material" refers to any cellulose raw material source that contains cellulose and that can be used in production of cellulose pulp, refined pulp, and fibril cellulose.

Plant material may be wood and said wood can be from softwood tree such as spruce, pine, fir, larch, douglas-fir or hemlock, or from hardwood tree such as birch, aspen, poplar, alder, eucalyptus or acacia, or from a mixture of softwoods and hardwoods. Non-wood material can be from agricultural residues, grasses or other plant substances such as straw, leaves, bark, seeds, hulls, flowers, vegetables or fruits from cotton, corn, wheat, oat, rye, barley, rice, flax, hemp, manilla hemp, sisal hemp, jute, ramie, kenaf, bagasse, bamboo or reed.

The cellulose raw material may be also derived from the cellulose-producing micro-organisms, such as from bacterial fermentation processes. The micro-organisms can be of the genus *Acetobacter, Agrobacterium, Rhizobium, Pseudomonas* or *Alcaligenes*, preferably of the genus *Acetobacter* and more preferably of the species *Acetobacter xylinum* or *Acetobacter pasteurianus*.

The term "cellulose pulp" refers to cellulose fibers, which are isolated from any cellulose raw material using chemical, mechanical, thermo-mechanical, or chemi-thermo-mechanical pulping processes.

Cellulose pulp of plant origin, especially wood (softwood or hardwood pulp, for example bleached birch pulp) and where the cellulose molecules are oxidized in one of the above-described methods, is easy to disintegrate to fibril cellulose using any mechanical disintegration methods.

The term "fibril cellulose" refers to a collection of isolated cellulose microfibrils (nanofibers) or microfibril bundles derived from cellulose raw material. Microfibrils have typically high aspect ratio: the length exceeds one micrometer while the number-average diameter is typically below 200 nm. The diameter of microfibril bundles can also be larger but generally less than 1 μm. The smallest microfibrils are similar to so called elementary fibrils, which are typically 2-12 nm in diameter. The dimensions of the fibrils or fibril bundles are dependent on raw material and disintegration method.

Fibril cellulose is characterized by very high water retention values, a high degree of chemical accessibility and the ability to form stable gels in water or other polar solvents. Fibril cellulose product is typically a dense network of highly fibrillated celluloses. The fibril cellulose may also contain some hemicelluloses; the amount is dependent on the plant source.

To obtain fibril cellulose mechanical disintegration of cellulose pulp or oxidized cellulose raw material is carried out with suitable equipment such as a refiner, grinder, homogenizer, colloider, friction grinder, ultrasound-sonicator, fluidizer such as microfluidizer, macrofluidizer or fluidizer-type homogenizer. Preferably mechanically disintegrated fibril cellulose is used.

Several different grades of fibril celluloses have been developed using various production techniques. The grades have different properties depending on the manufacturing method, degree of fibrillation and chemical composition. The chemical compositions of the grades also vary. Depending on the raw material source, e.g. HW vs. SW pulp, different polysaccharide composition exists in the final fibril cellulose product. Typically, non-ionic or native grades have wider fibril diameter while the chemically modified grades are a lot thinner. Size distribution is also narrower for the modified grades.

Fibril cellulose is understood to encompass here also any chemically or physically modified derivates of cellulose, fibril cellulose or nanofiber bundles, obtained from any plant based cellulose raw materials. The chemical modification may be based for example on carboxymethylation, oxidation, including TEMPO mediated oxidation, esterification, or etherification reaction of cellulose molecules. Modification may also be realized by physical adsorption of anionic, cationic, or non-ionic substances or any combination of these on cellulose surface. The described modification can be carried out before, after, or during the production of fibril cellulose. Certain modifications may lead to materials that are degradable in human body. Modified grades are typically prepared from bleached pulps. In the modified grades, the hemicelluloses are also modified together with the cellulose domain. Most probably, the modification is not homogeneous, i.e. some parts are more modified than others. Thus, detailed chemical analysis is not possible—the modified products are always complicated mixtures of different polysaccharide structures.

Chemically modified grades, particularly chemically or physically modified derivates, such as anionic and cationic grades typically have their surface charge modified and they may suitably be used as dry powder or an aqueous gel.

Dry powders of fibril cellulose may conveniently be manufactured by spray drying and/or lyophilization of suspension or dispersions containing said fibril cellulose, using any conventional methods known in the art. Suitably the chemically modified grades are spray dried and optionally granulated. These may be reconstituted into gel with water.

Suitably the cellulose raw material such as cellulose pulp is pretreated with acid and base prior to the mechanical disintegration. The pretreatment is effected by subjecting the cellulose pulp to acid treatment, preferably with hydrochloric acid for removing any positively charged ions having a charge more than +1, followed by treatment with an inorganic base containing positively charged ions having a charge +1, preferably NaOH, where $Na^+$ ions replace the earlier ions. The absence of any positively charged ions having a charge more than +1 is particularly advantageous in life science and molecular biology applications where complex formation of DNA with ions with charges more than +1 can be avoided. The pretreatment provides the final product excellent gelling properties and transparency. The fibril cellulose obtained from pretreated cellulose raw material is referred here to as ion exchanged fibril cellulose.

Microbial purity of fibril cellulose is often essential. Therefore, fibril cellulose may be sterilized prior to use, suitably in a gel form. In addition, it is important to minimize the microbial contamination of the product before and during the mechanical disintergration, such as fibrillation. Prior to fibrillation/mechanical disintegration, it is advantageous to aseptically collect the cellulose pulp from the pulp mill immediately after bleaching stage when the pulp is still sterile.

The "fibril cellulose" refers here to one grade or type of fibril cellulose or a combination of two or more different grades or types of fibril cellulose. For example chemically modified grades of fibril cellulose may be blended with native grade.

The fibril cellulose gel or hydrogel refers here to an aqueous dispersion of fibril cellulose. Fibril cellulose has excellent gelling ability, which means that it forms a hydrogel already at a low consistency in an aqueous medium.

Suitably plant derived fibril cellulose is used in the present invention.

The nutrient source is selected according to the specific requirements of each microbe, which is cultured. Particularly in bioleaching processes the nutrient source includes substrates selected from crushed metal ores to provide valuable metals, such as copper zinc, nickel, cobalt etc.

Optionally further additives well known to a man skilled in the art, generally used in microbial culture may be included in the composition, such growth factors, inorganic salts, antibiotics etc.

Plant derived fibril cellulose is suitably used as a hydrogel, which may be obtained also by reconstituting a dry powder prior to use by bringing it in contact with water. Particularly the modified grades, such as anionic and cationic grades, may be provided as dry products, such as powders, and hydrogels. The native and non-ionic grades are preferably provided as hydrogels.

The composition may be provided as a ready-to-use hydrogel, which may be pre-sterilized and packed in sterile packages, or it may be packed as a hydrogel for example in an applicator or container or syringe, which can be used for the application of the gel.

The number average fibril diameter of the fibril cellulose is suitably from 1 to 200 nm, preferably the number average fibril diameter of native grades is from 1 to 100 nm, and in chemically modified grades from 1 to 20 nm.

The composition comprises from 0.05 to 80 wt % of fibril cellulose. When the composition is a hydrogel, it may comprise from 0.05 to 5 wt %, suitably 0.1-3 wt % of fibril cellulose. A dried composition such powder may comprise higher amounts of fibril cellulose, typically up to approximately 95 wt %. The dry composition may be reconstituted with water prior to the use.

The composition may comprise 0.05-80 wt %, suitably 0.1-50 wt %, particularly 0.1-40 wt % of the nutrient source. Said nutrient source may comprise at least one of the following: carbon source, nitrogen source, phosphorus source, mineral source and trace element source. The high nutrient source refers particularly to bioleaching processes where the metal ore substrate is comprised in the nutrient source.

The composition may comprise water, suitably deionized or sterilized water depending on the culturing method. Suitably the fibril cellulose is blended carefully with water in order to prevent the formation of air bubbles and inclusion of air in the hydrogel.

Fibril cellulose hydrogels have typically high yield stress and high zero-shear viscosity at low concentrations. Thus, the hydrogels stabilize effectively solid particles against sedimentation, as is shown in example 6. The same physical features also prevent gas bubbles, possibly formed in the gel, rising from fibril cellulose hydrogels. The buoyancy of gas bubbles can be, however, easily increased by lowering gas pressure (e.g. 15 mmHg) above the gel, which lowers the solubility of gas in the hydrogels phase and, respectively increases the volumes of initial gas bubbles. The increased gas bubbles escape easily to upper gas phase while the cultured microbes remain in the gel phase. This pressure cycle may also be repeated if desire in order to collect the formed gaseous products.

Said hydrogel composition may further comprise additional components, depending on the microbes which are cultured.

The composition is obtainable with a method, which comprises the steps of

- providing fibril cellulose,
- mixing said plant derived fibril cellulose and optional nutrient sources and optional additives with water to obtain the composition. In the case a dry composition is made for reconstituting, an optional drying step is included.

Said composition may suitably be brought into contact with an inoculum of living microbe cells, where said microbes are selected from bacteria, yeasts, molds, and protozoa and transferred or placed to an environment for embedded culture of said microbes.

The invention also relates to a three-dimensional (3D) matrix comprising the composition comprising fibril cellulose, and living microbe cells, for embedded microbial culture.

The method of using fibril cellulose in a matrix for embedded microbial culture, comprises the steps of

- providing living microbe cells,
- providing a composition comprising fibril cellulose and optional nutrient sources and additives, culturing the cells in said composition in a 3D arrangement in an environment for embedded microbial culture.

The environment for embedded microbial culture refers to an environment where oxygen is removed from partly or totally.

The invention is further directed to a method for embedded 3D culture of microbes, said method comprising the steps of providing living microbe cells, where said microbes are selected from bacteria, yeasts, molds, and protozoa, contacting the microbe cells with a composition comprising fibril cellulose to form a 3D matrix, culturing the cells within said 3D matrix in a three-dimensional arrangement in an environment for embedded culture.

Additional components and nutrient sources in the composition, in the matrix and in the culturing method may be selected taking into account the requirements of the microbes in each case.

Further, the matrix containing fibril cellulose, as hydrogel, allows readily diffusion of small particles, which makes it possible to flush for example small viruses away with water. This diffusion effect is also exemplified in the examples.

Said composition is particularly suitable as a matrix or as a component in a matrix for embedded microbial culture for analytical methods, and in anaerobic and semi-anaerobic fermentation processes of microbes. Said fermentation processes may be batch operated or continuous and they may be carried out on a small scale or larger industrial scale and on very large scale, such as bioleaching processes, particularly in bioheaps. The composition may also suitably be used in large scale liquid or semi-liquid fermentation processes where industrial enzymes, starter cultures, etc are produced, and also in bioleaching processes. For example the nutrient source may be recirculated through the fermentor vessel.

Said composition and matrix may also be used for storage and transportation of microbes, and as immobilization matrix in fermentation processes, particularly of anaerobic microbes.

Fibril cellulose alone does not provide an adequate carbon source and thus alone it does not provide sufficient growth. However, the 3D structure improves microbial growth under suitable growth conditions. The 3D hydrogel structure provides for free molecular diffusion, sufficient support but on the other sufficient flexibility too.

After the process is completed it is easy to remove the remaining hydrogel material based on fibril cellulose from the cell growth material, for example using dilution with aqueous or non-aqueous liquid, followed by decantation, filtration or sedimentation using moderate centrifuging; or cellulose degrading enzymes, such as cellulases. In the case the cultured microbes are non-pathogenic it is also possible to use the remaining separated fibril cellulose material as animal feed.

The composition may be a in the form of ready-to-use hydrogel, which may be pre-sterilized and packed in sterile containers, packages, etc. or it may be pre-packed as a hydrogel for example in smaller containers or syringes, which can be used for the application of the gel. The viscosity of the hydrogel may easily be varied depending on the requirements of use.

Further, the composition may be incorporated in a kit, which may be used for example for analytical purposes. Such kit may comprise a transparent, thin and sealed container comprising pre-sterilized hydrogel, such as a small cuvette or a thin container having essentially greater length and height than the thickness. A microbe sample may be injected in said hydrogel, followed by incubation at anaerobic or semi-anaerobic conditions, suitable for said microbe sample, and the enumeration and detection may be carried out using any suitable methods, such as automatic visual methods if the microbes provide visual colonies (for example anaerobic *Chlostridium perfringens*), by UV or using PCR enumeration methods. It may be convenient to blend the microbe sample with a small amount of the hydrogel prior to the injection to the test container.

In the embedded culturing method the microbe cells are typically suspended homogenously into the continuous phase (hydrogel) due to mechanical support provided by the fibril cellulose fibers. The remarkably high yield stress stabilizes the microbial cells and the grown cell clusters against sedimentation.

Fibril cellulose hydrogels provide properties close to optimal particularly for 3D culturing:

transparent, non-toxic, non-animal based and highly viscous hydrogel have high suspending power, high water retention, good mechanical adhesion insensitive to salts, temperature or pH, not degradable under culturing conditions have no autofluorescence due to the chemical structure of the material dispensible, pumpable, injectable by syringe fibril cellulose is inert, and it does not interfere with analysis The matrix comprising fibril cellulose is also particularly suitable for storage and transportation of microbes, as well as an immobilization matrix for microbial fermentation and microbial enrichment, without any risk of potential detection or enumeration problems, particularly anaerobic microbes.

The quantification and enumeration of microbes is nowadays normally performed It is essential that the culture media does not comprise materials which interfere or inhibit the PCR reactions and make microbial quantification unreliable. The composition or matrix comprising fibril cellulose does not interact or inhibit PCR detection or PCR based microbial enumeration, comprising the use of real-time PCR (polymerase chain reaction) technique, where the microbes are broken down to release their DNA and the DNA is thereafter quantified by using specific oligonucleotide primers, thermostable DNA polymerase and appropriate thermal cycler. This is illustrated in the examples.

A significant advantage is that the culture media, composition or matrix comprising plant derived fibril cellulose can be injected or, on a larger scale pumped. This enables very easy handling and transferring of the material without the need to use mechanical measures, such as cutting etc. The injectability is explained by the unique rheological properties of plant derived fibril cellulose. The injection can be performed so that the cells stay stable inside the hydrogel or matrix and they are maintained homogeneously distributed in the hydrogel or matrix after injection or pumping. A small quantity or single colony can easily be picked up from the matrix for example by using sterile pipette, followed by characterization or analysis, which provides simple detection and uncomplicated colony isolation.

Further, the hydrogel does not disturb the molecular biology techniques often used for characterizing the isolated microbes. Anaerobic embedded culture of *Clostridium perfringens*, in a matrix comprising plant derived fibril cellulose hydrogel is illustrated in the examples.

The composition and the fibril cellulose hydrogel can be sterilized before hand and they can be cooled before use, thus making it possible to keep a stock of sterilized fibril cellulose hydrogel matrixes on shelves ready for use when desired. Therefore, for example laboratory workers can have stocks of sterilized fibril cellulose compositions on shelves. It is very convenient to mix a microbial sample in it and conduct incubation at suitable conditions for the microbial culture. This saves time and is very gentle to microbes. The fibril cellulose allows easy inoculation, good growth characteristics, particularly the softness of the fibril cellulose hydrogel allows good growth of microbes embedded in it.

The composition and matrix are also suitable in analytical and diagnostic applications, where laboratory robots are used, particularly preferably in anaerobic and semi-anaerobic culture of microbes.

According to one preferable embodiment the invention is particularly suitable for the culture of anaerobic bacteria, facultative bacteria, aerotolerant bacteria, protozoa, molds, and yeasts.

On a larger industrial scale microorganisms can be cultured in fermentation vessels in a culture medium comprising liquid components and solid components and the composition of the invention, or also in larger bioheaps in bioleaching processes.

The 3D hydrogel comprising fibril cellulose provides an excellent matrix for embedded anaerobic and semi-anaerobic culture of microbes, particularly culture of anaerobic bacteria, such as *Clostridium perfringens*. The invention provides also an excellent composition and matrix for the culture of several pathogenic organisms and soil microbes, which are often difficult to culture using conventional culture techniques. This is particularly useful also in the detection and characterization methods in the field of microbiology and diagnostics. Examples of such organisms are group A and B *Streptococcus, Staphylococcus aureus, Haemophilus influenzae, Helicobacter pylori, Acinetobacter baumannii, Coxiella bumetii, Bacillus anthracis, Francisella tularensis, Legionella pneumophila, Leptospira* species, *Klebsiella pneumoniae, Mycoplasma pneumoniae, Mycobacterium tuberculosis, Neisseria meningitides*, and examples of soil bacteria *Pseudomonas putida* and *Arthrobacter globiformis*.

EXAMPLES

The following examples are illustrative of embodiments of the present invention, as described above, and they are not meant to limit the invention in any way.

Materials and Methods a) Fibril cellulose samples. Native fibril cellulose was produced by high pressure homogenization (five subsequent cycles) of highly purified bleached birch pulp, followed by autoclave sterilization. After fluidization, the fibril cellulose was dilute hydrogel (1.8 wt %). Ion-exchanged native fibril cellulose was obtained in a similar manner but additionally prior to fibrillation it was subjected to acid-base treatment in order to remove high valency cations (method described in previous sections). After high pressure homogenization (15 subsequent cycles) the ion-exchanged fibril cellulose forms a strong hydrogel having lower turbidity compared to the other sample. Fibril cellulose was sterilized by autoclaving when necessary. Transparent anionic fibril cellulose was obtained as hydrogel (0.9 wt %) by similar homogenization process of a chemically modified cellulose pulp (TEMPO-oxidized cellulose pulp).

b) Microbial strains and cultivation. In all experiments fresh overnight cultures were used in the inoculation. The inoculation cultures did not contain fibril cellulose. The microbial cultivation was performed under optimal conditions and growth media. The microbial strain used was anaerobic gram positive *Clostridium perfringens* and the growth media was perfringens agar base.

c) Microbial detection. Microbial growth was detected visually when colony formation was noticeable. Perfringens agar base media with sodium metasulphite and ferric ammonium citrate produced black colonies in *Clostridium perfringens* cultures due to sulphite reduction. The cell numbers were also determined by quantitative PCR analysis (qPCR) as described in the following.

0.1 ml sample of the bacterial culture was used for PCR based microbial enumeration. The enumeration method was based on the Ruminolyze protocol, where the microbial sample is first diluted to washing buffer, and microbial cells were pelleted by centrifugation (10 min 18 000×g). The supernatant was discarded and pellet was suspended to enzymatic lysis buffer and thereafter strongly beaten with glass beads in order to both enzymatically and mechanically lyse microbial cells to release their DNA content. The released DNA was purified with phenol-chloroform extraction, then precipitated with ethanol and finally dissolved to the DNA storage buffer. The *Clostridium perfringens* enumerations were performed with two *Clostridium perfringens* selective DNA primers and Sybergreen I chemistry.

Example 1

Fibril Cellulose as a Sole Energy Source for Bacteria

The manufacturing processes of plant derived fibril cellulose may comprise steps that increase the risk for microbial contamination. Therefore, native fibril cellulose was tested for its capability to support microbial growth as a sole energy source. In FIG. 1 the fibril cellulose was challenged with *Clostridium perfringens* microbial contamination source, and the bacterial cell numbers in the beginning (0 h) and after overnight incubation on fibril cellulose are presented graphically. The reference bacterial cells were incubated on fibril cellulose (1.5 wt %) overnight and the bacterial cell numbers were counted. Furthermore, the extent of contamination was high, over $10^6$-$10^7$ cells/ml (Rough estimate of cell number can be calculated by dividing the 16S gene number by 10). The results clearly indicate that the bacteria strain had no growth on fibril cellulose. However, the control without any microbial inoculation shows high value in PCR analysis. It can be due to earlier contamination of dead microbes or it can be an artefact caused by cellulose fibrils. The fibril cellulose as a sole energy source does not support microbial growth effectively.

Example 2

Enumeration of Microorganisms from Fibril Cellulose Carrier

*Clostridium perfringens* bacterium was cultivated in two different media, one containing 1.5 wt % of native fibril cellulose and one without it. PCR based enumeration was used in the trial and it provided excellent example of fibril cellulose's interaction with the PCR detection.

Figure 2:
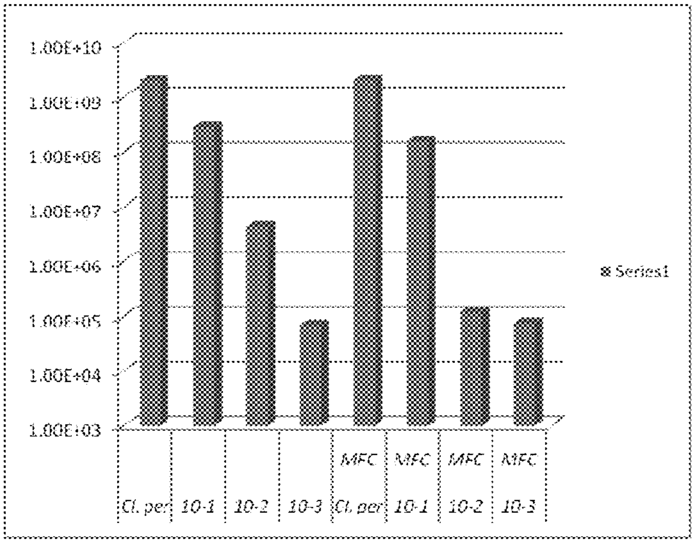
FIG. 2 illustrates graphically quantitative PCR run from *C. perfringens* dilution series showing strong linear correlation between the dilution and the PCR response in the presence or absence of 1.5 wt % plant derived fibril cellulose.

The growth medium used in the experiment was standard perfringens agar media, and it was prepared according the manufacturer's instructions and autoclaved for sterility. Before autoclaving the growth medium was divided into the two parts, one of which 1.5% by weight of fibril cellulose was added. Dilution series (10-, 100- and 1000-fold dilution) of dense *Clostridium perfringens* culture (about $10^9$ cells/ml) was prepared in the presence of 1.5% by weight of fibril cellulose and without it. Both test media were sampled 0 and 24 hours after the inoculation. 0.1 ml sample of culture was used for PCR based microbial enumeration. The enumeration method was based on the Ruminolyze protocol, where the microbial sample was first diluted to washing buffer, and microbial cells were pelleted by centrifugation (10 min 18 000×g). The supernatant was discarded and pellet was suspended to enzymatic lysis buffer and thereafter strongly beaten with glass beads in order to both enzymatically and mechanically lyse microbial cells to release their DNA content. The released DNA was purified with phenol-chloroform extraction, then precipitated with ethanol and finally dissolved to the DNA storage buffer. After the DNA isolation the DNA samples were used for PCR based enumeration by using *C. perfringens* specific primers and Sybergreen I chemistry. The results of PCR quantification are shown graphically in FIG. 2. The data shows strong linear correlation between PCR results and calculated dilution without any interference from fibril cellulose, i.e. between the dilution and the PCR response in the presence or absence of 1.5% by weight of fibril cellulose.

This experiment relating to quantitative PCR run from *C. perfringens* dilution series shows strong linear correlation between the dilution and the PCR response in the presence or absence of 1.5% fibril cellulose.

Example 3

Microbial Quantification in the Presence of Fibril Cellulose—Detection of Colonies Anaerobic and semi-anaerobic techniques are typically challenging to perform with current growth media and plating systems. As an example of anaerobic Gram positive bacteria of the clostridial species *Clostridium perfringens* can be mentioned where the growth is detected as black colonies.

Figure 3:
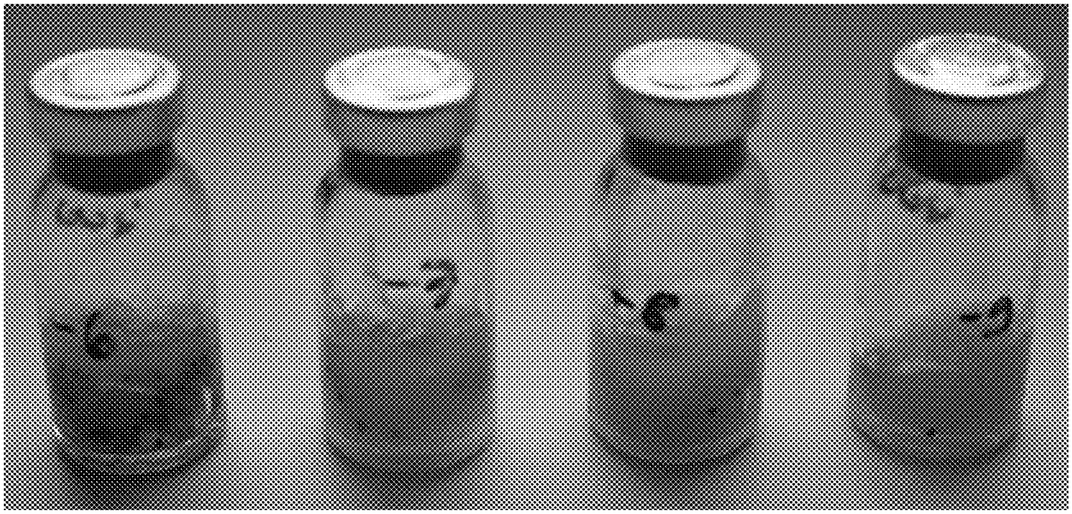
FIG. 3 illustrates microbial quantification of *C. perfringens* in the presence of fibril cellulose and detection of colonies.
Figure 4:
FIG. 4 illustrates *C. perfringens* dilution series cultivated in the combination of fibril cellulose and perfringens agar base media. *C. perfringens* colonies are visible as black dots.
Figure 5:
FIG. 5 illustrates *C. perfringens* dilutions. 10-8 dilution and 10-6 dilution in the combination of fibril cellulose and perfringens agar base media.

The clostridial species often require cultivation. There are challenges due to their strong sensitivity to oxygen. The present experiment describes a system that eases their culture by using a supporting matrix comprising fibril cellulose. Sterilized perfringens agar media (GROTH MEDIA) and native fibril cellulose (1.5 wt %) were sterilized in thick walled anaerobic serum bottles for long-term storage vessels for cultivations trials. The *C. perfringens* culture was diluted anaerobically and transferred by syringe and needle through the rubber vessel seal to the top of the medium. Thereafter the vessels were vortexed to mix the microbes and the media, and cultivated at an optimal temperature until clear growth of *C. perfringens* was visible. The *C. perfringens* was able to form black dot to the medium that could be easily calculated or even automatically registered by suitable instruments. In FIG. 3 *C. perfringens* dilution series cultivated in the combination of fibril cellulose and perfringens agar base media are presented. *C. perfringens* colonies are visible as black dots. FIGS. 4 and 5 show *C. perfringens* dilutions: 10-8 dilution and 10-6 dilution in the combination of fibril cellulose and perfringens agar base media. This technique was simple and fast for anaerobic microbial cultivation.

Example 4

Diffusion of Dextrans through Fibril Cellulose Hydrogels

Detailed knowledge on the diffusion properties of a cell culture material is important. The cell culture material should be porous enough to allow diffusion of nutrients and oxygen to the cultured cells as well as to enable efficient diffusion of metabolites from the cells. The diffusion properties of fibril cellulose hydrogel were demonstrated with different molecular weight dextrans in the following manner:

400 µl of anionic (oxidized) or native fibril cellulose (1%) was planted per filter on the apical compartment in Transwell™ filter well plates (filter pore size 0.4 µm). 1 ml of PBS was added into the basolateral side and 100 µl (25 µg) of fluorescent labeled dextrans were added on top of the hydrogels (MW of 20k, 70k and 250k). Plate was fixed firmly and left undisturbed on a well plate rocker. 100 µl samples were taken from the basolateral side and equal amount was replaced with PBS. First samples were taken with 15 minute intervals, other samples were taken with different time points ranging from 30 minutes to 2 hours and final samples at 24 hours. Total of 168 samples were taken. Target plate (OptiPlate™-96 F) was measured at excitation and emission wavelengths 490 nm and 520 nm respectively.

Figure 6:
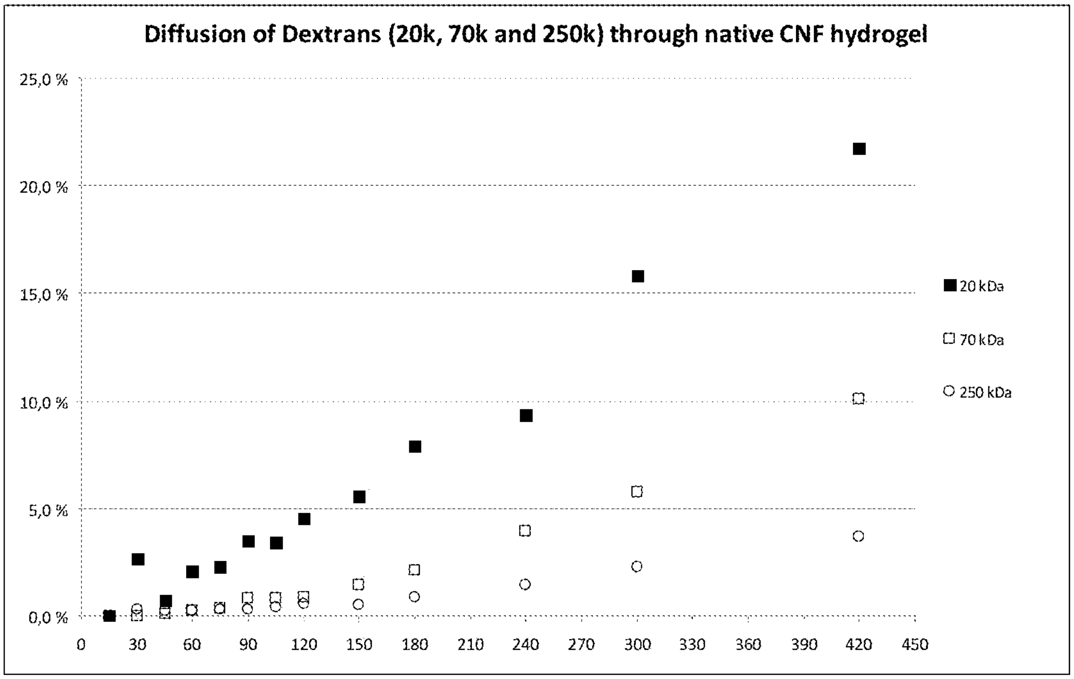
FIG. 6 depicts diffusion of different molecular weight dextrans (20 kDa, 70 kDa, and 250 kDa) through 1% native cellulose nanofiber hydrogel.

Diffusion of different molecular weight dextrans through 1% native cellulose nanofiber gel is presented in FIG. 6. The diffusion of the model compounds takes place at constant rate and it is highly dependent on the molecular weight (size) of the compound. It is clear that in the fibril cellulose hydrogels molecules are able to diffuse efficiently although the gel structure is firm enough to stabilize the cell suspension.

Example 5

Flow Properties of Fibril Cellulose Hydrogel

The rheological flow properties of fibril cellulose hydrogels show several features that are beneficial in the cell culture use. The hydrogels have a high viscosity at low shear (or rest) for optimum suspending capacity of the cells but also show shear-thinning behavior at higher shear rates to enable easy dispensing and injection. The ability of fibril cellulose to provide these kinds of rheological properties was demonstrated in a test series where the viscosity of fibril cellulose dispersions was measured over a broad shear stress (rate) range in a rotational rheometer (AR-G2, TA Instruments, UK).

Figure 7:
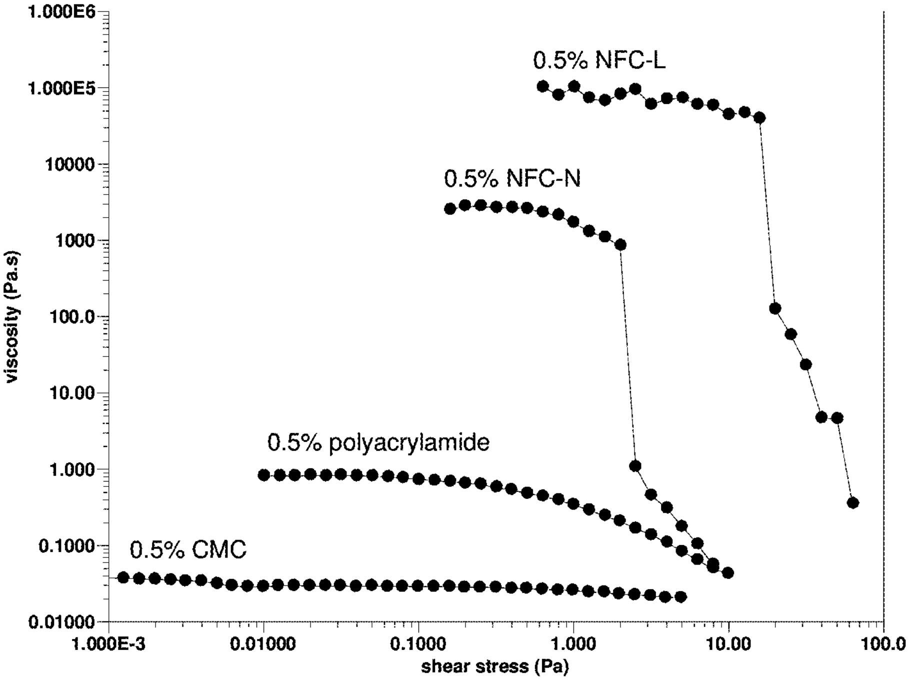
FIG. 7 depicts viscosity of 0.5% fibril cellulose hydrogels as function of applied shear stress in comparison with 0.5% solution of water soluble polymers polyacrylamide (5 000 kDa) and CMC (250 kDa).

Fibril cellulose dispersions show much higher zero-shear viscosities (the region of constant viscosity at small shear stresses) than other water soluble polymers, as shown in FIG. 7. The zero-shear viscosity of fibril cellulose is greatly increased by smaller nanofibril diameter induced by preceding chemical pretreatment of the starting material. The stress at which shear-thinning behavior starts ("yield stress") is also considerably high for the fibril cellulose dispersions. The suspending ability of a material is the better the higher the yield stress. The cells are effectively stabilized against sedimentation by the combined effects of high zero-shear viscosity and high yield stress and high storage modulus. The gravitational force applied by the cells is much weaker than the yield stress. Thus, the suspended cells are "frozen" inside the gel matrix if mixing with fibril cellulose or "frozen" on the gel if deposited on the top of the gel.

Figure 8:
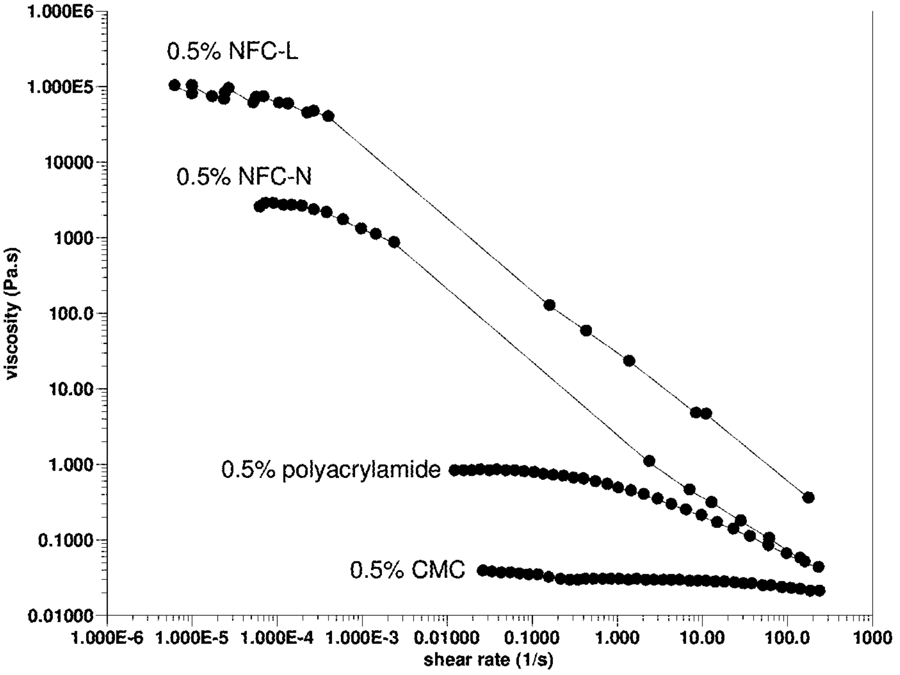
FIG. 8 depicts viscosity of 0.5% CNF hydrogels as function of measured shear rate in comparison with 0.5% polyacrylamide and CMC. Typical shear rate regions of different physical processes have been marked on the figure with arrows.

In FIG. 8 the viscosity is presented as a function of the measured shear rate. From this FIG. 6 it is obvious that the viscosity of the fibril cellulose dispersions drops at relatively small shear rates and reaches a similar level as that measured for the reference materials at shear rates of about 200 s-1.

Figure 9:
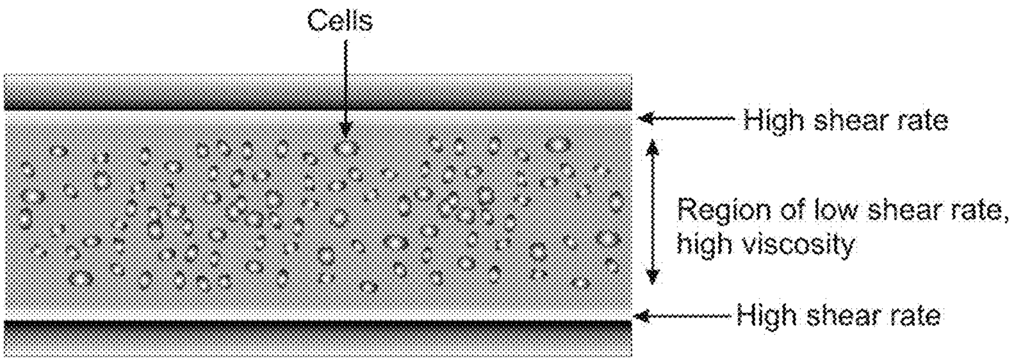
FIG. 9 depicts schematic presentation of fibril cellulose hydrogel containing cells, flowing in a needle. High shear rate region (low viscosity) is located at the gel-needle interface and low shear rate region (very high viscosity) is located in the middle of the needle.

The network structure of fibril cellulose breaks down upon shearing (FIG. 8). Upon the application of a certain stress, the viscosity of the system drops dramatically and a transition from solid-like to liquid-like behavior occurs. This kind of behavior is beneficial as it enables mixing of the cells homogeneously into the fibril cellulose suspension by moderate mechanical shearing. When two-phase liquids, such as flocculated fibril cellulose dispersions, are sheared (e.g. in a rheometer or in a tube), the dispersed phase tends to move away from the solid boundaries, which leads to the creation of a lower-viscosity layer of liquid at the walls of the container (FIG. 9). This phenomenon means that the resistance to flow, i.e. the viscosity is lower at the boundaries than in the bulk of the dispersion. Respectively, injection of the fibril cellulose hydrogel with a syringe and a needle or with pipette is easy even at high concentrations (1-4%). The phenomenon enables also easy dispensing of cell suspensions with minimum disturbance of the cells, i.e. majority of the cells are located in the middle of the needle and are practically at rest (FIG. 9).

Example 6

Stability

Even very dilute dispersions of fibril cellulose have a very high viscosity at low shear rates. The hydrogel structure is also recovered when shear, such as injection, ceases. At static conditions, fibril cellulose forms a hydrogel network with high elastic modulus and exceptionally high yield stress. Due to these properties, fibril cellulose has a very high suspending power of solid particles even at very low concentration.

Figure 10:
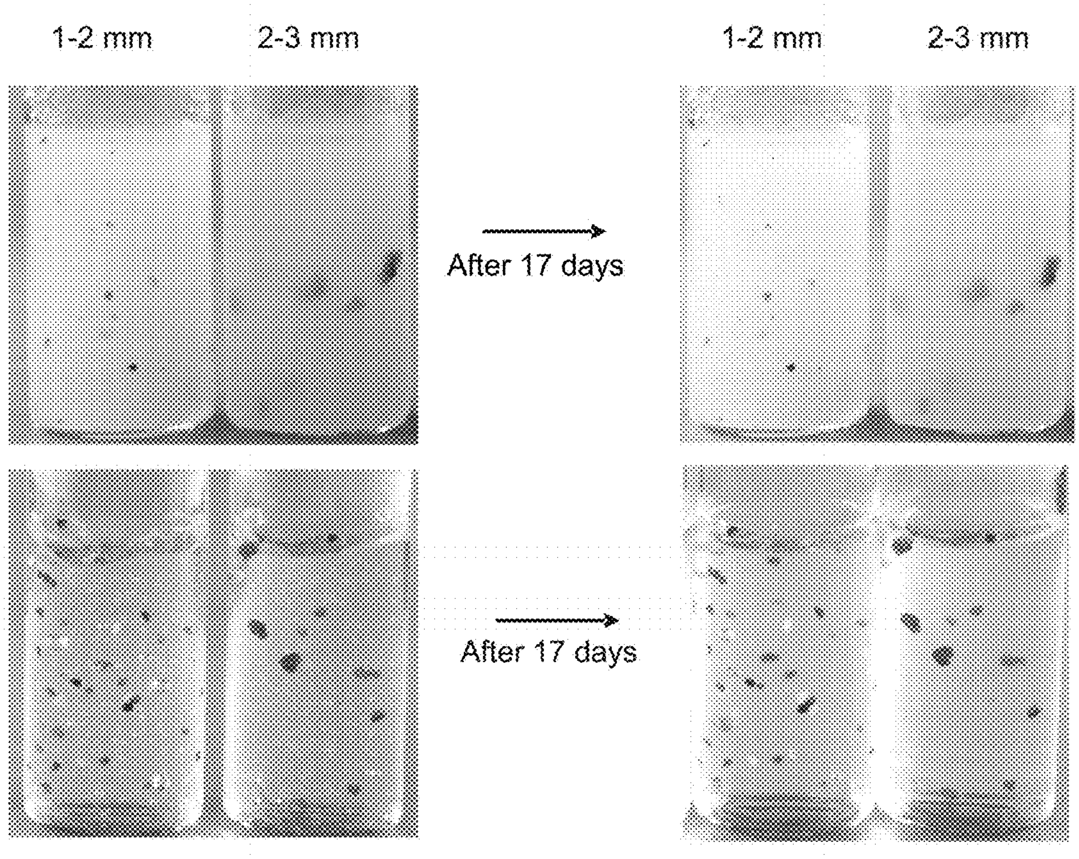
FIG. 10 depicts stability of two gravel suspensions in 0.5% native fibril cellulose hydrogel, (top row) and in 0.5% anionic fibril cellulose hydrogel (bottom row) for 17 days period. The gravel was CEN Standard sand (EN 196-1) with average particle size 1-2 mm and 2-3 mm. The samples were stored at room temperature.

The suspending ability at static conditions is demonstrated with gravel suspensions. 0.5% dispersions of native fibril cellulose and anionic fibril cellulose are able to stabilize even 2-3 mm size gravel particles for very long periods of time, see FIG. 10. It should be noted that the anionic fibril cellulose is able to stabilize particle suspensions at lower concentration than native fibril cellulose.

While the invention has been described with respect to specific examples including presently preferred modes of carrying out the invention, those skilled in the art will appreciate that there are numerous variations and permutations of the above described embodiments that fall within the spirit and scope of the invention. It should be understood that the invention is not limited in its application to the details of construction and arrangements of the components set forth herein. Variations and modifications of the foregoing are within the scope of the present invention.

The invention claimed is:

1. A composition for embedded three-dimensional microbial culture, said composition comprising:

mechanically disintegrated plant derived nanofibrillar cellulose and at least one nutrient source, wherein the composition comprises 0.05-80 wt % of nanofibrillar cellulose, the composition being in the form of hydrogel, and wherein the composition has a liquid viscosity upon shearing such that the composition is dispensable, pumpable, or injectable; and a plurality of microbes suspended homogenously in the composition.

2. The composition according to claim 1, wherein the nanofibrillar cellulose is selected from native nanofibrillar celluloses and chemically modified nanofibrillar celluloses.

3. The composition according to claim 1, wherein the nanofibrillar cellulose is native ion-exchanged nanofibrillar cellulose.

4. The composition according to claim 1, wherein the composition comprises water and optional additives.

5. The composition of claim 1, wherein the nanofibrillar cellulose is configured to form a stable gel in a polar solvent.

6. The composition of claim 1, wherein the nanofibrillar cellulose is partly covered with hemicellulose polysaccharides.

7. The composition of claim 1, wherein the at least one nutrient source includes one or more metal ores.

8. The composition of claim 1, wherein the plurality of microbes include bacteria configured to convert insoluble metal compounds in the at least one nutrient source to water-soluble metal compounds.

9. A composition for microbial culture, said composition comprising:

mechanically disintegrated plant derived nanofibrillar cellulose in the form of a three-dimensional matrix;

at least one nutrient source; and a plurality of microbes suspended homogenously in the composition, the composition being in the form of a hydrogel, wherein the composition has a liquid viscosity upon shearing such that the composition is dispensable, pumpable, or injectable.

10. The composition of claim 9, wherein the composition comprises 0.05-80 wt % of the nanofibrillar cellulose.

* * * * *